United States Patent [19]

Stillwagon et al.

[11] Patent Number: 4,849,885
[45] Date of Patent: Jul. 18, 1989

[54] THERMOGRAPH WITH COMPUTER DISPLAY

[76] Inventors: W. Glenn Stillwagon; Kevin L. Stillwagon, both of 773 Dry Run Rd., Monongahela, Pa. 15063

[21] Appl. No.: 580,606

[22] Filed: Feb. 16, 1984

[51] Int. Cl.⁴ .......................... G06F 15/42; A61B 5/00
[52] U.S. Cl. ............................. 364/413.1; 364/413.02; 364/413.13; 128/736; 358/113
[58] Field of Search ............... 364/413, 415, 417, 557, 364/413.1, 413.01, 413.13; 250/330–334; 128/736

[56] References Cited

U.S. PATENT DOCUMENTS

| | | | |
|---|---|---|---|
| 3,830,970 | 8/1974 | Hurley et al. | 250/330 X |
| 3,868,508 | 2/1975 | Lloyd | 250/330 |
| 4,010,367 | 3/1977 | Suzuki | 250/334 |
| 4,055,166 | 10/1977 | Simpson et al. | 128/736 X |
| 4,186,748 | 2/1980 | Schlager | 128/736 |
| 4,218,707 | 8/1980 | Reed et al. | 358/113 |
| 4,366,381 | 12/1982 | Fischer et al. | 250/332 X |
| 4,379,461 | 4/1983 | Nilsson et al. | 128/736 |
| 4,428,382 | 1/1984 | Walsall et al. | 128/736 |
| 4,445,516 | 5/1984 | Wollnik et al. | 128/736 |
| 4,461,301 | 7/1984 | Ochs | 128/736 X |

*Primary Examiner*—Gary V. Harkcom
*Attorney, Agent, or Firm*—Webb, Burden, Ziesenheim & Webb

[57] ABSTRACT

An apparatus detects and displays a thermograph and comprises a hand-held scanner carriage having a plurality of spaced infrared sensors pointed in the same direction. Electronic circuits select and digitize the analog inputs of each infrared sensor at spaced time intervals. A computer logs the digitized data and displays a thermograph being a representation of the digitized data on a cathode ray tube (CRT) or the like.

13 Claims, 7 Drawing Sheets

THERMOGRAPH WITH COMPUTER DISPLAY

DESCRIPTION

BACKGROUND OF THE INVENTION

There exists a need in the chiropractic, medical and para medical fields for a relatively inexpensive thermograph apparatus that can instantly display color coded representations of the temperature over some area of the human body. The general health of an individual readily affects skin temperature. Inflammation or other abnormal conditions results in higher than normal temperatures. Physiologists have determined that the temperature of the skin can vary widely. Advance medical, paramedical and surgical techniques for treatment of diseased or damaged areas of a patient make use of thermographs, that is, two dimensional representations of the temperature over an area of the body. In this way, the locations of the areas to be treated are identified. The conditions causing the abnormal temperatures can then be managed by a method chosen by the treating doctor or specialist.

Prior devices for recording thermographs have either been very large and too expensive for dedication to a practitioner's office or have provided insufficient data and in a form not easily used.

The applicants' invention is based, at least in part, upon the fact that the practitioner can easily learn to draw a paddle supporting a plurality of aligned and spaced infrared temperature sensors over an area of the body at a correct uniform rate while data is gathered at spaced intervals. Thus complicated rocking mirror devices used in prior art two-dimensional thermograph apparatus can be avoided. Also, the readings can be taken by sensors that are spaced only a short distance, say, one-quarter to one inch from the area of the body under consideration notwithstanding the contour of the body thus increasing the precision of the readings. Since it is often the temperature distribution that is important as much as the actual temperatures, it is useful to be able to quickly display a color coded thermograph illustrating the temperature distribution. It is an advantage of the applicants' invention to provide such a display on a color television screen.

SUMMARY OF THE INVENTION

Briefly according to this invention, there is provided an apparatus for detecting and displaying a thermograph. The apparatus comprises a handheld paddle or scanner carriage having a plurality of spaced infrared sensors pointed in the same direction. The apparatus further comprises an electronic circuit for selecting and digitizing the analog outputs of each infrared sensor at spaced time intervals. The apparatus further comprises a computer device for logging the digitized data and processing the data for color coded display. The apparatus further comprises a color television or cathode ray tube (CRT) display which, in response to the output of the computer device, presents a thermograph.

According to this invention there is provided a method for analyzing disorders and memorializing treatment by use of the above described apparatus for detecting and displaying a thermograph. The method comprises a first step of taking an initial or first scan by drawing the paddle (which is a hand-held scanner carriage) over the area of the human body to be evaluated and studied; taking at least one more scan following treatment and storing data in mass storage for future reference.

More specifically, an apparatus for infrared thermography and analysis is provided. The apparatus includes a microcomputer having a CPU (central processing unit), main memory and data and address buses interconnecting the CPU and main memory. The apparatus comprises an analog input board for sequentially digitizing a plurality of analog inputs and for passing the digitized signal to the data bus of the microcomputer under the command of the microcomputer. The apparatus comprises a hand-held paddle for supporting a plurality of infrared sensors spaced along an axis. The sensors provide the analog input to the analog input board. Thus the paddle can be drawn over the area of the anatomy that is of interest along a selected axis (say, the spine) keeping the axis of the paddle perpendicular to the selected axis. The apparatus comprises a device for mass storage memory associated with the computer and controlled by the computer, for example, a floppy disk drive. The apparatus comprises a color CRT associated with the computer and under the control thereof. The apparatus has stored in main memory a first task for preparing a file on the mass storage device for data storage; a second task for capturing a matrix of digitized data input from the analog input board as the hand-held paddle is drawn over an area of the anatomy; a third task for displaying the matrix of digitized data color coded on the color CRT and a fourth task for saving the matrix of digitized data in a file on the mass storage memory device.

It is preferred, according to this invention, that the analog input board comprise a binary counter which outputs on a multi-bit digital signal automatically to poll the analog inputs from the infrared sensors and to select address locations in a cache memory located on the analog input board for saving at least one row of digitized data corresponding to the polled input. Preferably, the analog board has a two input multiplexer for permitting either the binary counter or the computer address bus to control of the cache memory. The analog input board continually polls the sensors and updates the cache memory. At spaced intervals the computer interrupts the analog input process and unloads a row of digitized data stored in the cache memory moving it to a location in a matrix in the computer's main memory. In a special embodiment, the task for displaying the matrix of digitized data stored in the computer memory comprises construction of a second data matrix wherein each matrix element stores a value indicative of a temperature range. A color is assigned to each temperature range and a thermograph is displayed on a colored CRT corresponding to the second matrix by causing picture elements (pixels) to display said colors.

According to a very preferred embodiment, the paddle has an additional infrared sensor which is directed substantially differently than the plurality of spaced sensors thus enabling a temperature reading at just one location to be made. The main memory has stored therein a task for reading that temperature from the cache memory on the analog input board and displaying a numeric representation thereof on the CRT. It is also a most preferred embodiment that the magnitude of the temperature ranges can be selected so that the precision of the color representation over a gross temperature range can be adjusted.

THE DRAWINGS

Further features and other objects and advantages of this invention will become clear from the following detailed description made with reference to the drawings in which.

DESCRIPTION OF THE PREFERRED EMBODIMENTS

Figure 1:
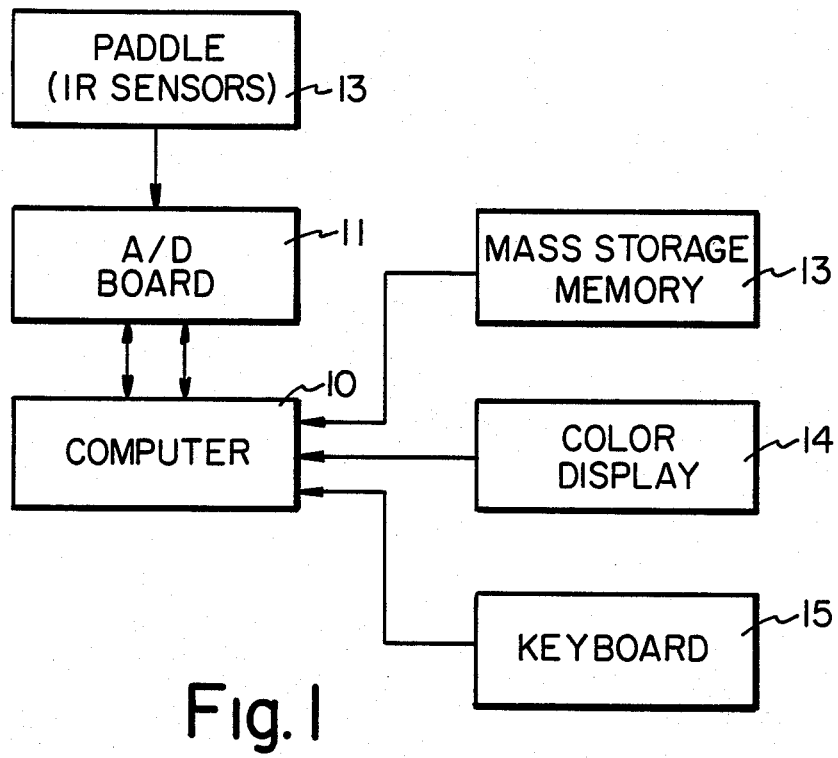
FIG. 1 is a function diagram of the entire system according to this invention.

Referring not to FIG. 1, there is illustrated in function diagram form the system according to this invention. The system comprises a microcomputer 10 having a CPU (central processing unit), main memory, address, data, and control buses. Connected to the microcomputer by the address, data and control buses is an analog input board 11. The analog input board is designed to digitize and capture analog data from a plurality of infrared sensors mounted in paddle 13 which paddle may be hand-held. Associated with the computer is a mass storage memory device 13, such as floppy disk drive, and a color display 14 such as a color CRT or a color plotter. A keyboard 15 permits manual input to the system.

The purpose of the system is to generate an infrared thermograph. The specific use for which the system was designed and developed was thermographic study of a patient's spine, for example, by a chiropractor to analyze the disorder, if any, and to plan the chiropractic adjustment appropriate to the disorder. In this case, use by a chiropractor, it is useful to display a plurality of thermographs side-by-side to illustrate the disorder and resulting correction of that disorder.

Figure 2:
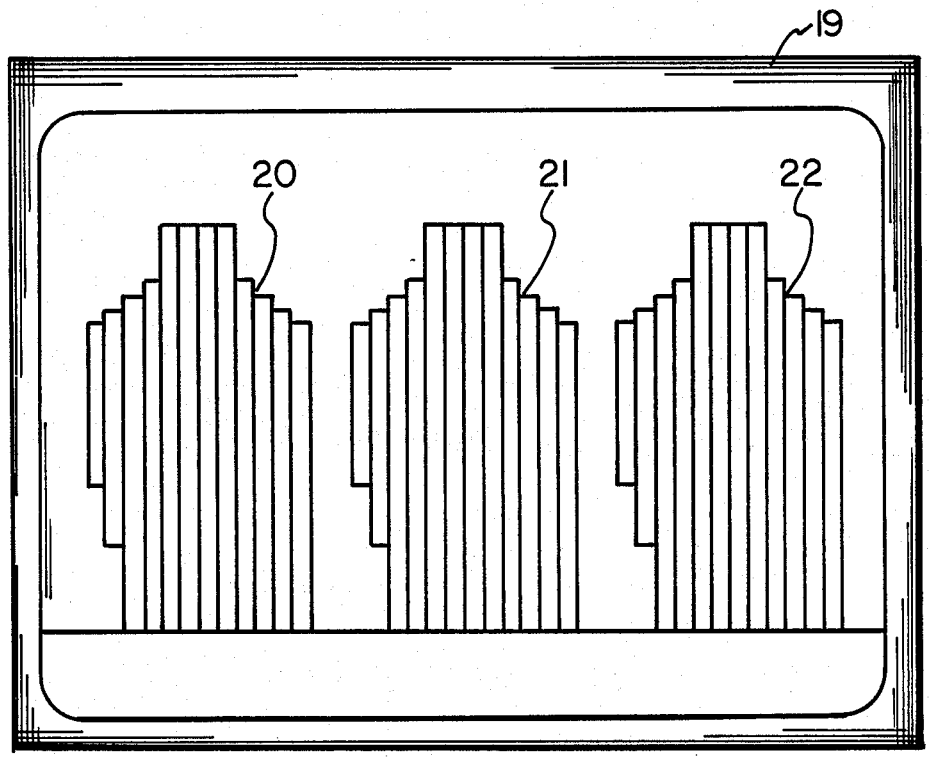
FIG. 2 is a representation of a display generated by the system according to this invention.

FIG 2 illustrates on a CRT display 19 (but, of course, not in color) what might be generated by use of this system. The display comprises the thermographs 20, 21, 22 of the general area of the neck, shoulders, upper and lower back along the spine. Each picture element (pixel) within a given thermograph is colored differently depending upon the temperature of the skin at the corresponding location on the patient's back. The number of pixels may vary but in one embodiment of this invention, the thermograph display has 864 pixels arranged 12×72.

Figure 3:
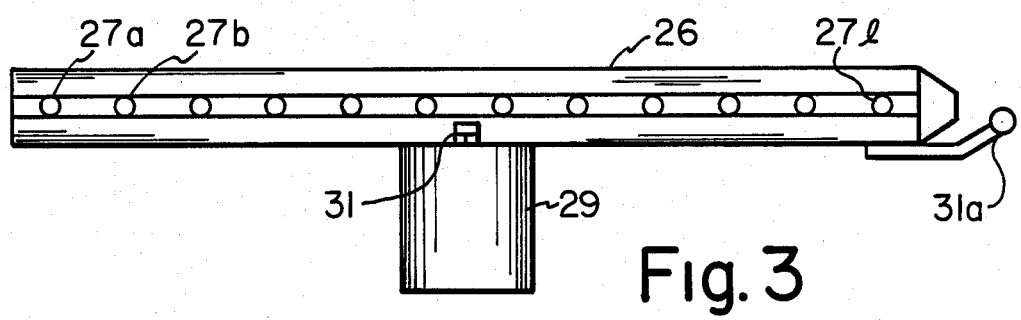
FIG. 3 is a front view of an infrared sensor paddle.
Figure 4:
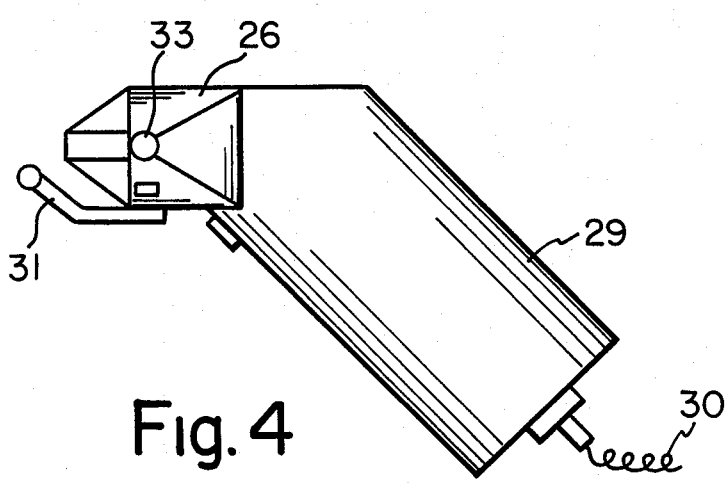
FIG. 4 is a left-side view of an infrared sensor paddle shown in FIG. 3.

A temperature reading is required for each pixel in the thermograph. The temperatures are gathered by drawing the paddle along the spine under the instructions of the system. Referring to FIGS. 3 and 4, there is illustrated a paddle suitable according to this invention. The paddle comprises a bar 26 approximately twelve inches long having a plurality (12 shown) of infrared sensors 27a, 27b, ... 27l equally spaced along the bar and pointed in the same direction. The number of infrared sensors on the bar is, of course, a matter of design. The greater the number of sensors the wider the area that can be swept by the paddle if the spacing is retained the same. The closer the spacing, of course, the greater the precision up to a point. This, of course, depends upon the focussing ability of the infrared sensors and the area observed considering that the sensor is maintained spaced from the surface being scanned. Suitable infrared sensors are sensitive in the temperature range 80° to 110° F. (27° to 43° C.). Infrared light emitted from the body is known to have a wave length in the range of 0.5 to 30 μm (microns). A suitable infrared sensor is sold under the trade name Barnes Thermopile Detector. It has an active sensing area of 1×1 mm and a standard acceptance angle of 72°. It provides spectral coverage from 0.6 to 35 μm. It is available in small TO-5 cases. The impedance of the detector is approximately 8000 ohms making it suitable for use with integrated circuits. The sensor comprises six junction pairs formed of vacuum deposited thin films of dissimilar conductors. One junction in each pair is a reference in thermal conduct with a heat sink. The measurement junctions are blacked, thermally isolated from the heat sink, thus free to absorb (or emit) radiation. The resulting temperature rise (or fall) causes a voltage to appear across the junction. The junction pairs are connected in series to produce a voltage of 15 volts per watt for incident radiation. Extending away from the bar 26 is a hand grip 29, a cable 30 enters one end of the hand grip. The cable carries at least one lead wire to each infrared sensor and a ground wire. The paddle may be provided with a spacer 31 and 31a that controls the distance between the paddle and the surface being scanned. According to a preferred embodiment, the paddle is provided with an extra infrared sensor 33 pointed in a different direction than the sensors 27. This sensor is used for the determination of a temperature at but one location.

Figure 5:
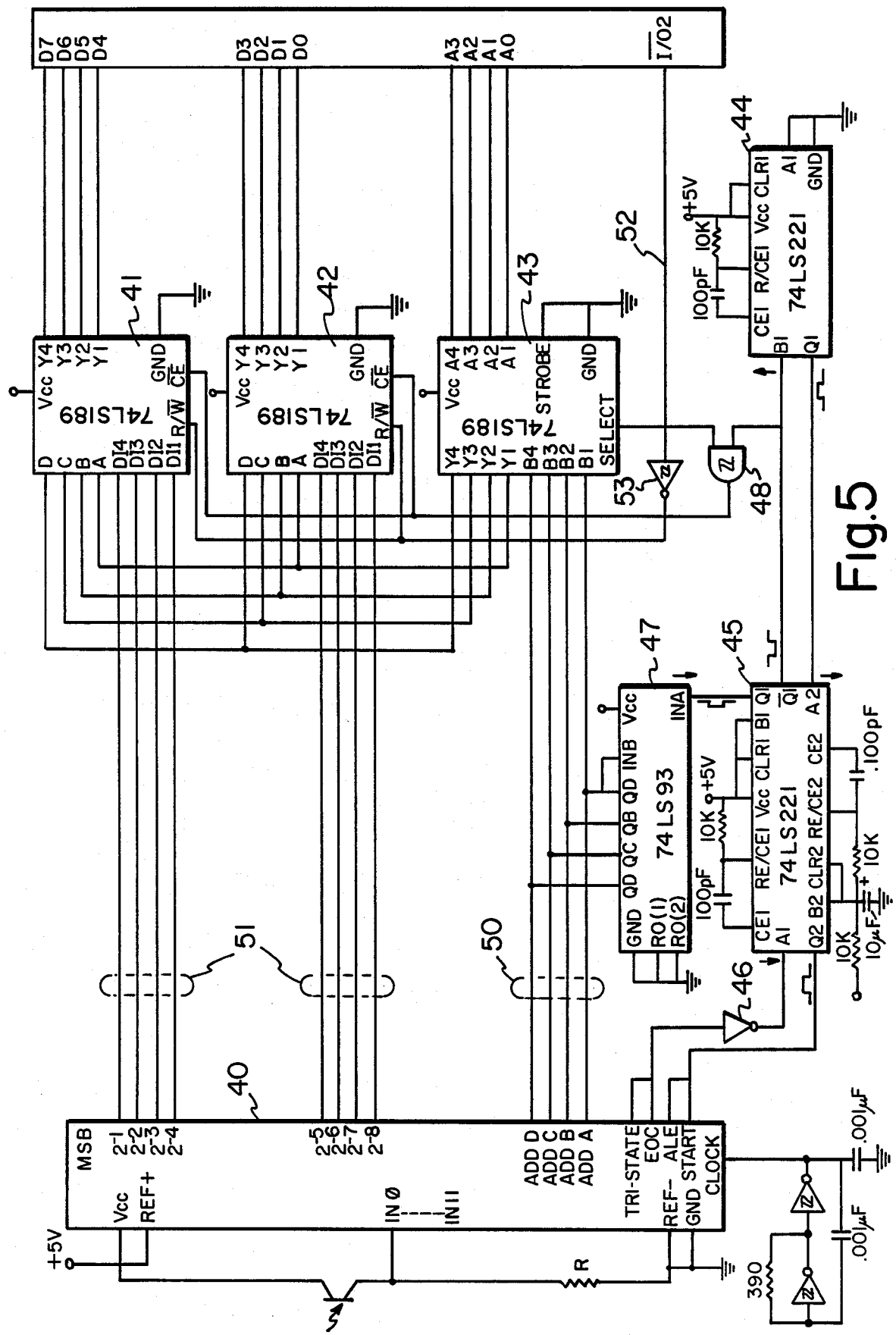
FIG. 5 is a detailed schematic of the analog input board.

Referring now to FIG. 5, the analog input board 11 is a special purpose circuit board in communication with the address, data and control buses of the CPU. FIG. 5 schematically illustrates the essential integrated circuit chips on the board and the interconnection thereof. The heart of the board is an analog to digital chip 40 that multiplexes up to 12 analog inputs, IN0 ... IN11, any of which may be selected by a signal on the input board internal address bus 50. The output of the chip 40 is an eight-bit digitized signal on the input board internal data bus 51.

The analog input board has thereon a cache memory comprising, for example, two 74LS189 memory chips 41 and 42 for capturing the output of the chip 40 corresponding to one reading of each infrared sensor on the paddle. The analog input is selected by binary counter 47 which drives the internal address bus 50. Counter 47 is clocked by the falling edge of the output pulse $Q_1$ of the dual monostable multi-vibrator 45. The four-bit binary output of the binary counter 47 is applied to the chip 40 to select the analog input and through a two input multiplexer 43 to the address inputs of the memory chips 41, 42. In normal operation, the analog input lines are continuously polled, the analog values digitized, and the digitized values stored in the cache memory chips 41, 42.

A positive pulse from the $Q_2$ output of the second half of chip 45 (74LS221—dual nonstable multi-vibrator) is applied to the analog input chip 40 at terminal START and terminal ALE to initiate the digitizing of data from the sensor designated by the signals upon the internal address bus 50. When the digitizing procedure is complete the EOC output of the chip 40 goes high. This pulse is inverted in Schmitt trigger 46 and is applied to the clocking input $A_1$ of the first half of chip 45. The falling edge of the output of the Schmitt trigger 46 starts the outputs $Q_1$ and $\overline{Q}_1$ of the one shot multi-vibrator (chip 45). Output $\overline{Q}_1$ of chip 45 immediately goes negative thereby enabling the memory chips 41 and 42 for a write to the memory byte addressed by the signals still upon the internal address bus 50. The enable signal is processed through the AND gate 48 which is arranged to operate as a negative logic OR gate. At this moment, the digitized data is written. When $Q_1$ out of the first half of chip 45 falls it clocks the 4 bit binary counter 47 to increment the address on the internal address bus. At the same instance, the enable signal goes positive disabling the memory chips. The rising edge of $\overline{Q}_1$ of the one shot chip 45 now clocks one shot chip 44 to start positive going delay pulse at $Q_1$ of chip 44. This delay pulse is applied to the clocking input $A_2$ of the second half of chip 45. The falling edge of the delay pulse clocks the second side of chip 45 to cause the output $Q_2$ to go positive and thus to restart the digitizing chip 40. The delay pulse permits a time for the signal on the internal address bus 50 to settle before the next analog device is read and digitized.

When the CPU needs to read the cache memory, the memory requests line 52 is pulled low and the signal is applied directly to the select input of the two input multiplexer 43, thus giving the system address bus control of the address inputs to the cache memory. The signal on the memory requests line is processed through a Schmitt trigger 53 to put the memory chips 41 and 42 in the read mode. At the same time, the memory request signal is fed to AND gate 48 to enable the cache memories 41 and 42.

The CPU may be any suitable microcomputer. The particular one being described is built from a Commodore 64 Home Computer which has a 6510 microprocessor chip therein. Details of the Commodore 64 system may be found in the "Commodore 64 Programmer's Reference Guide" (1982). The keyboard and video output are standard for the Commodore 64 and the disk drive is that provided for the Commodore 64. The analog board interfaces the Commodore 64 through the expansion port.

To this point, the apparatus according to this invention has been described. The description now turns to the tasks or programs stored in the computer memory which cooperate with the apparatus to provide the applicants' unique infrared thermograph.

Figure 8:
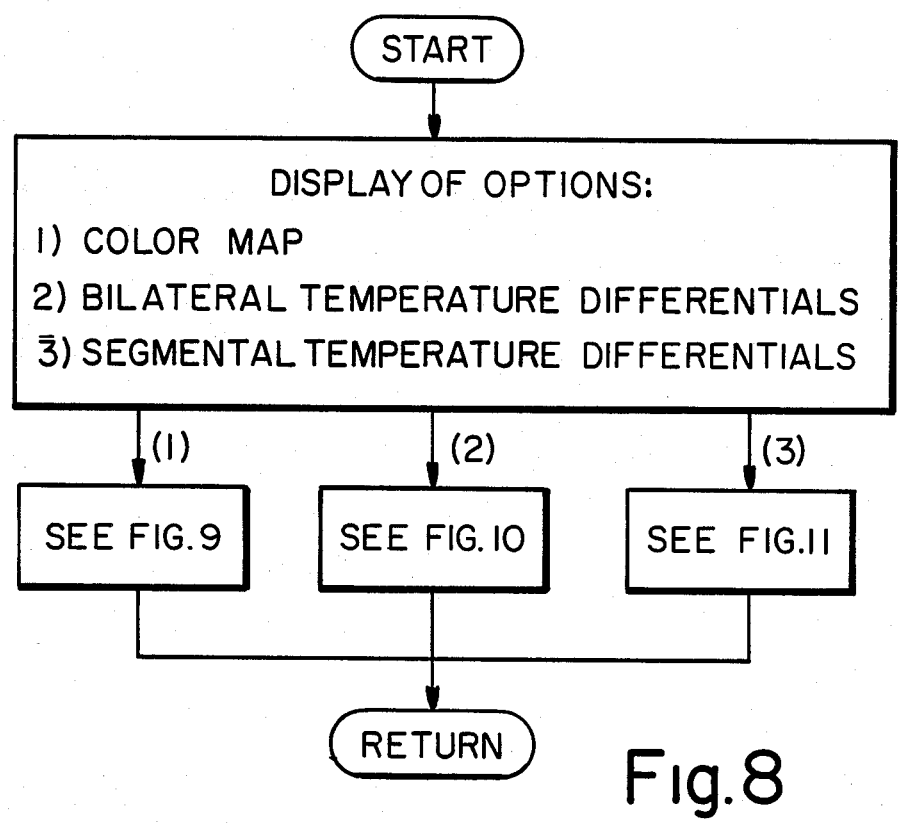
FIG. 8 is a flow diagram describing the task for selecting a data display option.
Figure 6:
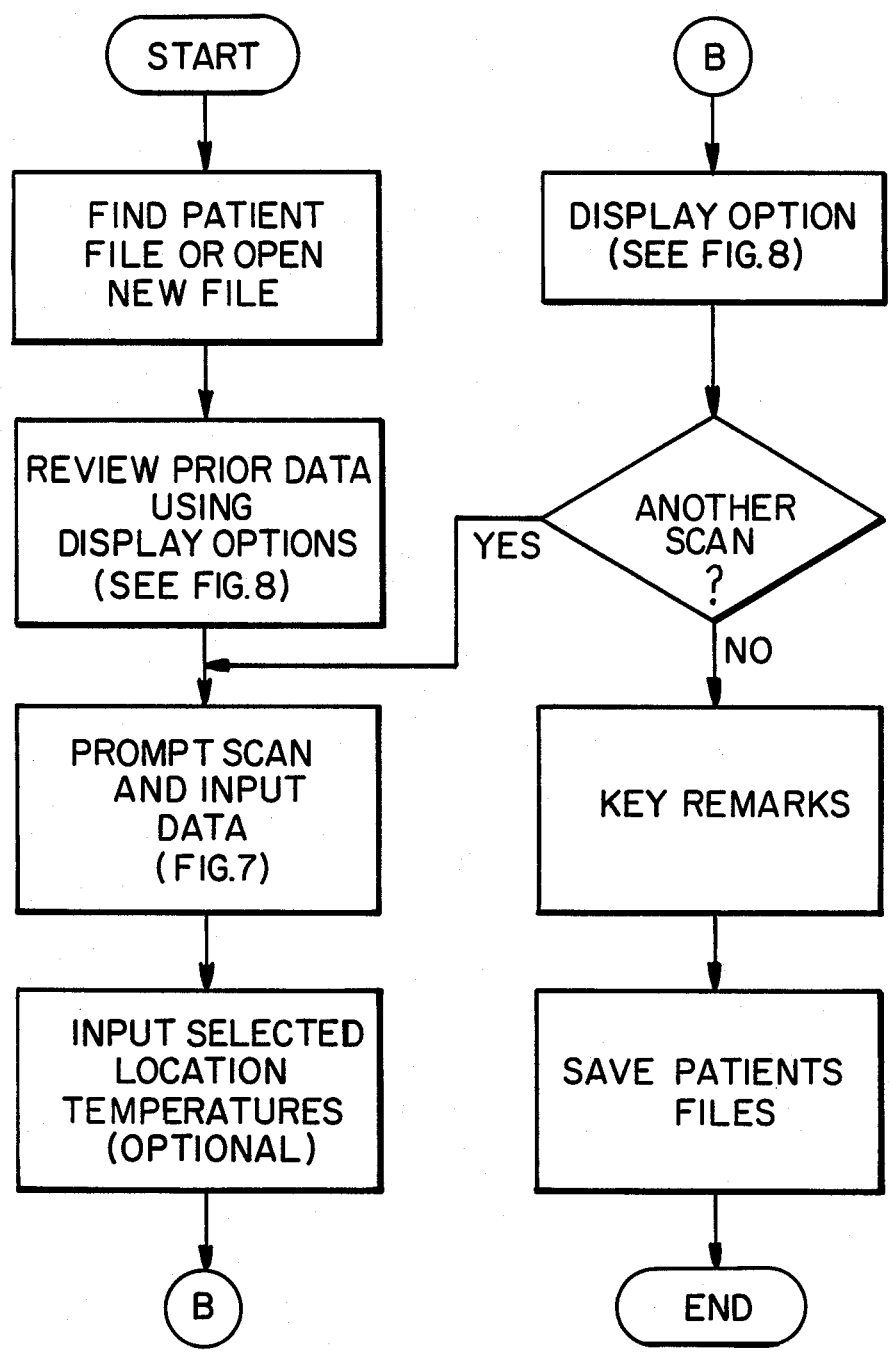
FIG. 6 is a flow diagram describing the overall tasks stored in main memory according to this invention.

Referring now to FIG. 6, the main task stored in main memory will be described. The main task begins with a step for finding the patient's file or opening a new file on the mass storage device. Data in the existing file, if any, is then available for display. A step for receiving in the existing patient file and for using the various display options described with reference to FIG. 8 is provided. The next step in the main task is prompting the drawing of the paddle over the patient and inputting row data from the paddle through the analog input board. The details of this subtask are described with reference to FIG. 7. The main task then permits the input of a selected reference temperature from the sensor 33 through the analog board.

Now the main task provides for display of the just gathered data matrix using one of the display options (see FIG. 8). At this point, the main task permits repeat of the scan and data input step. (FIG. 7) Up to three scans may be input and simultaneously displayed as thermographs on the CRT. For example, the first thermograph may be displayed at the leftmost position 20 on the CRT (see FIG. 2), the next thermograph in the middle position 21 and the third thermograph at the right position 22. If no further scans are to be made, text may be added to the patient file relating to the three scans just taken. Finally, all data is saved in the mass storage medium. This concludes the cycle of the main task.

Figure 7:
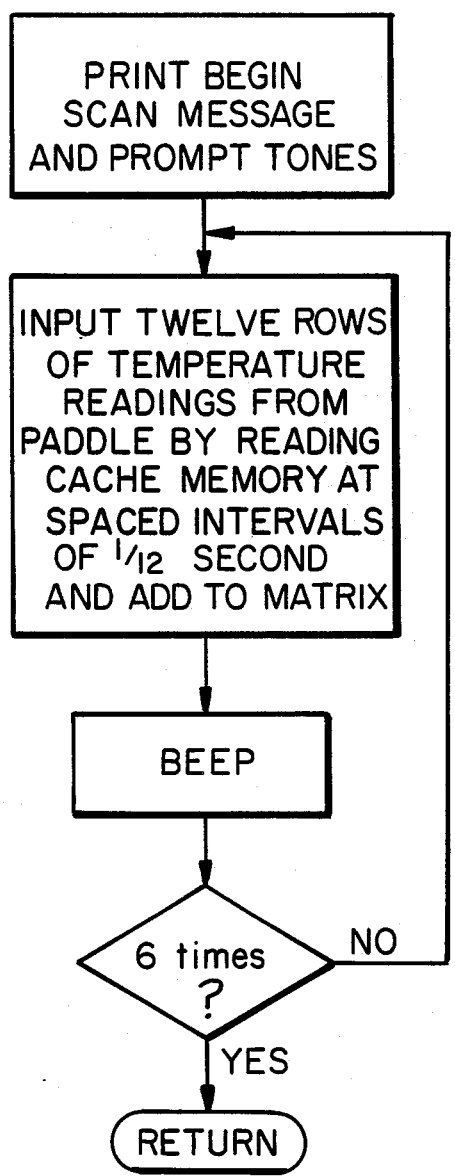
FIG. 7 is a flow diagram describing a task for prompting the use and inputting a digitized data matrix.
Figure 10:
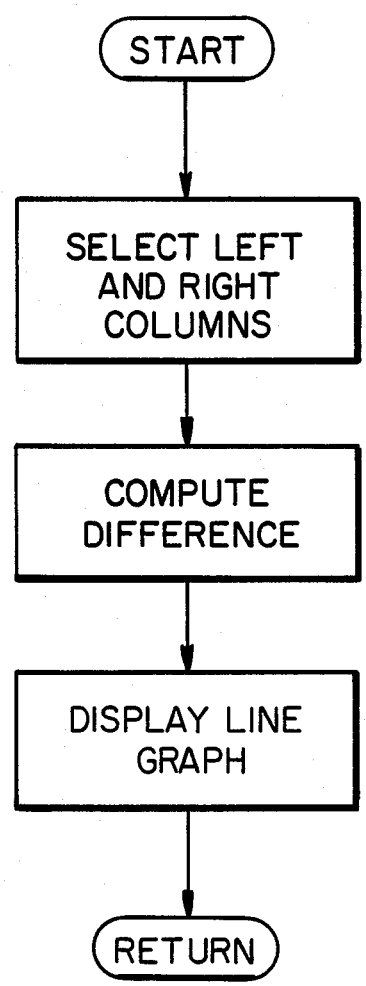
FIG. 10 is a flow diagram describing the task for displaying a line graph of bilateral temperature differentials.

Referring now to FIG. 7, the subtask for prompting the user and inputting digitized data is described. Preferably, a message is first printed on the CRT indicating that the data gathering procedure is about to commence and then audible signals such as five low tones followed by an intermediate tone are sounded to prompt the user to begin drawing the paddle across the area to be studied commencing with the intermediate tone. The analog input board continuously inputs rows of digitized infrared temperature data and stores the data in the cache memory on the input board. The new row of digitized data is written over the old row in the cache memory whether or not any use has been made of the data in the cache memory. At spaced intervals, the computer gains control of the cache memory and reads a row of digitized data into a first matrix in main memory. Referring to a preferred embodiment, the computer reads the cache memory every one-twelfth second or twelve times per second. To aid the user in drawing the paddle across the area of study at the correct speed, a high tone (beep) is emitted by the computer every one second. According to a preferred embodiment of this invention, the data gathering procedure takes place over a period of six seconds thus seventy-two rows of data are gathered. Since each row contains twelve infrared sensor readings the first matrix contains 864 temperature readings.

Referring now to FIG. 8, there is shown a flow diagram of a subtask for enabling selection of one of three display modes. The options available are a color map, a line graph of bilateral temperature differential and a line graph of segmental temperature differentials. Selection of a particular display mode cause a call of the particular display task therefor.

Figure 9:
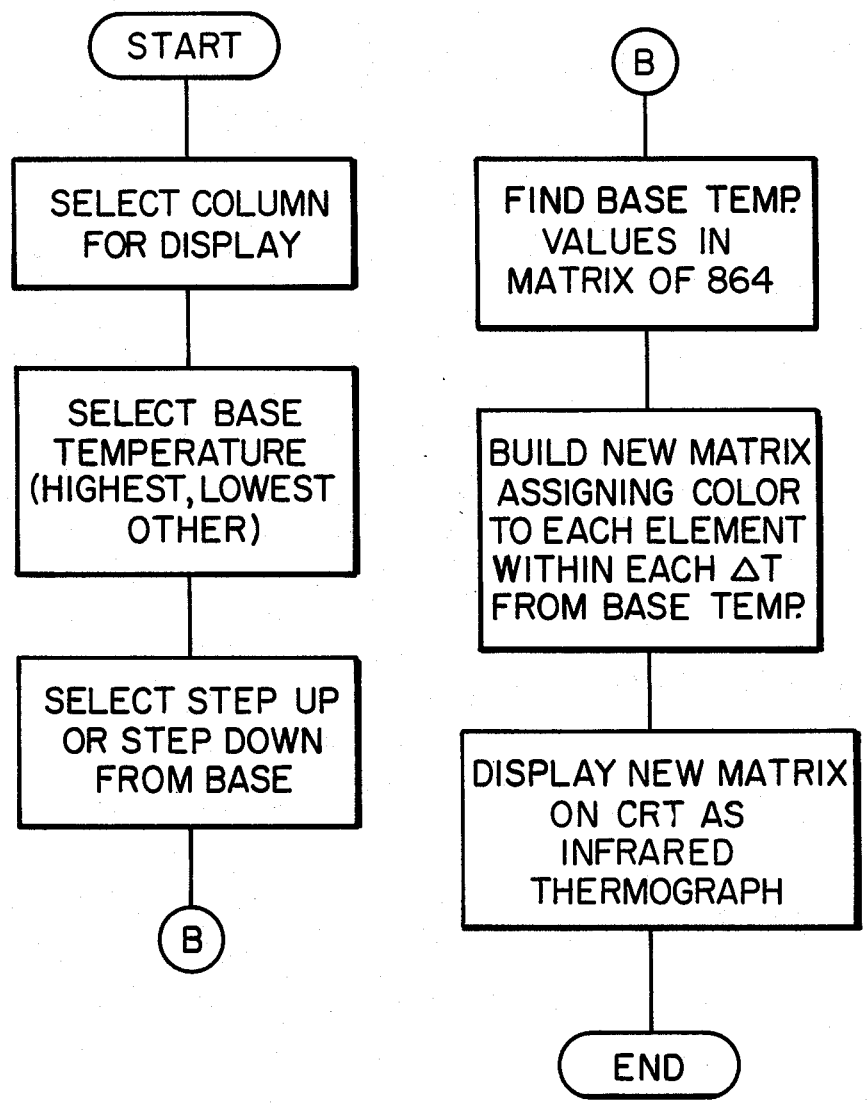
FIG. 9 is a flow diagram describing the task for displaying a color coded thermograph.

Referring now to FIG. 9, there is shown a flow diagram of the subtask for displaying a thermograph on the colored CRT. The first step is finding the base temperature in the first matrix. The base temperature may be the highest temperature in the matrix, the lowest temperature in the matrix or a selected temperature (for example, selected by the input from sensor 33). The next step is building a new matrix assigning a new code for each one degree of temperature change below the warmest temperature. The color codes may be assigned as follows: white for the warmest; followed by dark red, light red, green, light blue, dark blue and gray for the coldest. Black is assigned any temperature below gray. The new matrix is then mapped to the CRT as an infrared thermograph.

Figure 11:
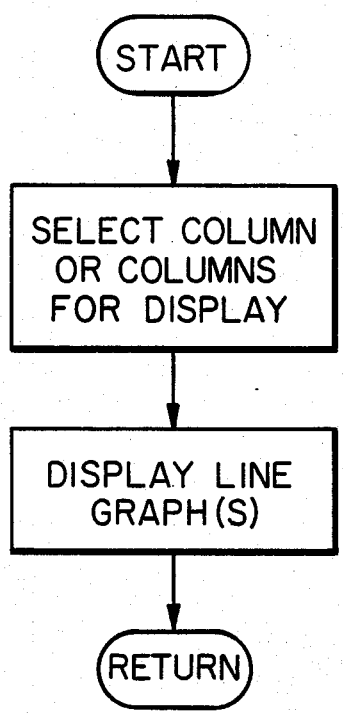
FIG. 11 is a flow diagram describing a task for displaying a graph of one column of digitized data (segmental temperature differential).

Referring now to FIG. 11, a display of a segmental differential temperature graph, in the form of a line graph, is made by use of this optional subtask. The operator first selects one or two columns for display, that is, one or two of the twelve columns generated by an earlier scan. The task then builds tables and displays it as a line or lines showing the temperature profile of the selected column or columns. This subtask works directly with the first matrix containing the digitized analog data input from the analog board.

Having thus described our invention in the detail and particularity required by the Patent Laws, what is desired protected by Letters Patent is set forth in the following claims.

The invention claimed is:

1. An apparatus for detecting and displaying a thermograph of an area of study comprising:
    (a) a hand-held scanner carriage having a plurality of spaced infrared sensors arranged in a single row and pointed in the same direction,
    (b) means for selecting and digitizing the analog inputs of each infrared sensor at spaced time intervals to produce a row of digitized data,
    (c) means for logging the row of digitized data in a two-dimensional data matrix wherein the first dimension of the data matrix is sensor position upon the scanner carriage and the second dimension of the data matrix is time as the carriage is being continuously drawn over the area of study, and
    (d) means for displaying a thermograph comprising a representation of the two-dimensional data matrix.

2. The apparatus according to claim 1 wherein the logging means and display means comprises a general purpose digital computer.

3. The apparatus according to claim 1 wherein the displaying means produces a two-dimensional color coded display of the digitized data.

4. An apparatus for infrared thermography and diagnosis of an area of the human anatomy comprising:
    (a) a microcomputer having a central processing unit, main memory, data bus, control bus, and address bus,
    (b) an analog input board for sequentially digitizing a plurality of analog inputs and for passing the digitized data to the data bus of the microcomputer,
    (c) a hand-held paddle for supporting a plurality of infrared sensors spaced along an axis, said sensors providing the analog inputs to the analog input board, wherein said paddle can be drawn over the area of the anatomy that is of interest in a direction substantially perpendicular to the axis of the spaced sensors,
    (d) a device for mass data storage associated with said microcomputer,
    (e) a display means associated with said microcomputer,
    (f) said main memory having stored therein
        (i) a task for preparing a file on the mass storage memory device for data storage,
        (ii) a task for capturing a matrix of digitized data as the hand-held paddle is drawn over the surface to be diagnosed in which columns of the matrix are gathered by one of said sensors and rows of the matrix are gathered by all of said sensors,
        (iii) a task for displaying data captured in the matrix of digitized data on the display means, and
        (iv) a task for saving the matrix of digitized data in a file on the mass storage device.

5. An apparatus according to claim 4 wherein the display is a color display and wherein the task for displaying data captured in the matrix of digitized data comprises construction of a second data matrix wherein each matrix element stores a value indicative of a temperature range, assigning a color code to each temperature range and displaying a thermograph comprising a graphic representation of the second matrix on said color display by causing picture elements to display said colors.

6. An apparatus according to claim 5 wherein the magnitude of the temperature ranges can be selected.

7. An apparatus according to claim 5 wherein a plurality of thermograph matrices can be displayed simultaneously upon the CRT.

8. An apparatus according to claim 5 wherein the task for displaying data captured in the matrix of digitized data comprises selection of two columns of data within the matrix and construction of a difference column wherein the elements of the difference column are the difference between the corresponding elements in the selected columns and display of the data in the difference column upon the display means as a graph of bilateral temperature differentials.

9. An apparatus according to claim 5 wherein the task for displaying data captured in the matrix of the digitized data columns comprises selection of one column of data within the matrix and display of the data from that column upon the display means as a graph of segmental temperature differentials.

10. An apparatus for infrared thermography and diagnosis of an area of the human anatomy comprising:
    (a) a microcomputer having a central processing unit, main memory, data bus, control bus, and address bus,
    (b) an analog input board for sequentially digitizing a plurality of analog inputs and for passing the digitized data to the data bus of the microcomputer, said analog input board comprises a cache memory and a counter which outputs a multi-bit digital signal automatically to poll the analog inputs and to select address locations in the cache memory for saving digitized data corresponding to the polled input,
    (c) a hand-held paddle for supporting a plurality of infrared sensors spaced along an axis, said sensors providing the analog inputs to the analog input board, wherein said paddle can be drawn over the area of the anatomy that is of interest in a direction substantially perpendicular to the axis of the spaced sensors,
    (d) a device for mass data storage associated with said microcomputer.
    (e) a display means associated with said microcomputer,
    (f) said main memory having stored therein
        (i) a task for preparing a file on the mass storage memory device for data storage,
        (ii) a task for capturing a matrix of digitized data as the hand-held paddle is drawn over the surface to be diagnosed in which columns of the matrix are gathered by one of said sensors and rows of the matrix are gathered by all of said sensors,
        (iii) a task for displaying data captured in the matrix of digitized data on the display means, and
        (iv) a task for saving the matrix of digitized data in a file on the mass storage device.

11. An apparatus according to claim 10 wherein the analog board has a two input multiplexer for giving either the binary counter or the microcomputer address bus control of the cache memory.

12. The apparatus according to claim 11 wherein the task for capturing the matrix of digitized data comprises, at spaced intervals, inputting a row of digitized data from the cache memory to a first matrix in main memory.

13. An apparatus according to claim 10 wherein the paddle has an additional infrared sensor associated therewith which is substantially differently directed than the plurality of sensors such that a temperature reading at just one location can be taken.

* * * * *

UNITED STATES PATENT AND TRADEMARK OFFICE
CERTIFICATE OF CORRECTION

PATENT NO. : 4,849,885

DATED : July 18, 1989

INVENTOR(S) : W. Glenn Stillwagon and Kevin L. Stillwagon

It is certified that error appears in the above-identified patent and that said Letters Patent is hereby corrected as shown below:

Column 1 Line 50 "handheld" should read --hand-held--.

Column 3 Line 33 "not" should read --now--.

Claim 10 Line 54 Column 8 "." should read --,--.

Signed and Sealed this

Tenth Day of April, 1990

Attest:

HARRY F. MANBECK, JR.

Attesting Officer

Commissioner of Patents and Trademarks